(12) United States Patent
Giovanoli et al.

(10) Patent No.: US 9,289,913 B2
(45) Date of Patent: Mar. 22, 2016

(54) PUNCHING DEVICE WITH MODULAR PUNCHING MEANS

(75) Inventors: Nando Giovanoli, Bivio (CH); Reto Menzi, Filzbach (CH)

(73) Assignee: Hamilton Bonaduz AG, Bonaduz (CH)

( * ) Notice: Subject to any disclaimer, the term of this patent is extended or adjusted under 35 U.S.C. 154(b) by 0 days.

(21) Appl. No.: 14/113,901

(22) PCT Filed: Apr. 29, 2012

(86) PCT No.: PCT/EP2012/057871
§ 371 (c)(1),
(2), (4) Date: Oct. 25, 2013

(87) PCT Pub. No.: WO2012/146769
PCT Pub. Date: Nov. 1, 2012

(65) Prior Publication Data
US 2014/0102275 A1    Apr. 17, 2014

(30) Foreign Application Priority Data
Apr. 29, 2011  (DE) .......................... 10 2011 075 035

(51) Int. Cl.
*G01N 1/08* (2006.01)
*G01N 1/28* (2006.01)
(Continued)

(52) U.S. Cl.
CPC ... *B26D 5/08* (2013.01); *B26F 1/02* (2013.01); *B26F 1/14* (2013.01); *G01N 1/286* (2013.01);
(Continued)

(58) Field of Classification Search
CPC ........... G01N 1/04; G01N 1/286; G01N 1/08; G01N 35/0099; G01N 2035/00039
USPC ...................................................... 73/864.41
See application file for complete search history.

(56) References Cited

U.S. PATENT DOCUMENTS

| 3,972,260 | A |   | 8/1976 | Hayashi et al. |        |
|-----------|---|---|--------|----------------|--------|
| 4,821,614 | A | * | 4/1989 | Fleet et al.   | 83/100 |

(Continued)

FOREIGN PATENT DOCUMENTS

| DE | 689 07 958 T2 | 1/1994 |
|----|---------------|--------|
| DE | 693 08 957 T2 | 9/1997 |

(Continued)

OTHER PUBLICATIONS

International Search Report from PCT/EP2012/057871 dated Jul. 4, 2012, 2 pgs.

(Continued)

*Primary Examiner* — Paul Hyun
(74) *Attorney, Agent, or Firm* — Rothwell, Figg, Ernst & Manbeck, PC

(57) ABSTRACT

A punching device is provided for processing samples applied to a sample card comprising at least one punching head with a punch and a lower die, the punch being movable between a resting position and a punching position. The punching head has a receiving opening into which a sample card can be introduced by a movable gripping unit, and a punching drive, which drives the movement of the punch between the resting position and the punching position. A piece of sample punched out from the sample card can be discharged at an outlet opening of the lower die into a receiving recess of a receiving container. The punching head comprises a structure separate from the punching device, wherein the structure of the punching head forms an exchangeable module that is couplable to the punching device and the punching drive.

16 Claims, 6 Drawing Sheets

(51) Int. Cl.
  *B26D 5/08* (2006.01)
  *B26F 1/02* (2006.01)
  *G01N 35/00* (2006.01)
  *B26F 1/14* (2006.01)

(52) U.S. Cl.
  CPC .. *G01N 35/0099* (2013.01); *G01N 2035/00326* (2013.01); *Y10T 83/207* (2015.04); *Y10T 83/2209* (2015.04); *Y10T 83/6576* (2015.04)

(56) References Cited

U.S. PATENT DOCUMENTS

| | | | |
|---|---|---|---|
| 4,979,415 A | 12/1990 | Kakimoto | |
| 5,641,682 A | 6/1997 | Pagels et al. | |
| 2007/0293789 A1 | 12/2007 | Lehinen | |
| 2008/0107500 A1* | 5/2008 | Cheng et al. | 412/16 |
| 2009/0139353 A1 | 6/2009 | Kline et al. | |
| 2011/0132111 A1* | 6/2011 | Shoemaker et al. | 73/864.41 |
| 2011/0232451 A1* | 9/2011 | Liu et al. | 83/685 |
| 2011/0263038 A1* | 10/2011 | Morrison et al. | 436/174 |

FOREIGN PATENT DOCUMENTS

| | | | |
|---|---|---|---|
| DE | 600 28 352 T2 | 3/2007 |
| EP | 0 287 986 A2 | 10/1988 |
| EP | 0349887 A2 | 1/1990 |
| GB | 1505556 A | 3/1978 |
| GB | 2414700 A | 12/2005 |
| JP | S63-267195 A | 11/1988 |
| JP | H05-77940 U | 10/1993 |
| WO | 9512482 A1 | 5/1995 |
| WO | 00/57153 A1 | 9/2000 |
| WO | 2006056658 A1 | 6/2006 |
| WO | 2008/003693 A1 | 1/2008 |
| WO | 2008013331 A1 | 1/2008 |
| WO | 2009035182 A1 | 3/2009 |
| WO | 2009105810 A1 | 9/2009 |
| WO | 2010/009173 A1 | 1/2010 |

OTHER PUBLICATIONS

German Search Report from 10 2011 075 035.5 dated Apr. 13, 2012, 8 pgs.
Notice of Reasons for Rejection issued in copending Japanese Patent Application No. 2014-506903, 13 pages (Oct. 6, 2014).
Office Action (with English translation) issued in copending Chinese Patent Application No. 2012800207186, 12 pages (Jan. 28, 2015).
Search Report issued in copending Chinese Patent Application No. 2012800207186, 3 pages (Jan. 19, 2015).
PerkinElmer Inc., "Punch intelligently with the Wallace DBS Puncher," Clinical Screening, PerkinElmer Life and Analytical Sciences, Shelton CT, USA, 1296-967-04U, printed in Finland, 2 pages (Feb. 2005).
Notice of Reasons for Rejection with English translation issued in copending Japanese Patent Application No. 2014-506903, 5 pages (Jul. 17, 2015).

* cited by examiner

PUNCHING DEVICE WITH MODULAR PUNCHING MEANS

CROSS REFERENCE TO RELATED APPLICATION

This application is a 35 U.S.C. 371 National Phase Entry Application from PCT/EP2012/057871, filed Apr. 29, 2012, which claims the benefit of German Patent Application No. 10 2011 075 035.5 filed on Apr. 29, 2011, the disclosure of which is incorporated herein in its entirety by reference.

The present invention relates to a punching device for processing dried samples applied to a sample card, in particular of liquids containing DNA such as blood, saliva and the like.

In such punching devices, a plurality of sample cards are kept in a magazine for sample cards and are removed from the magazine in a particular order by means of a gripper unit and fed to a punching means of the punching device. In an area, previously captured by means of imaging methods, in which the applied sample has been identified on the sample card, at least one sample piece is then punched out of the sample card. It is also possible for a plurality of sample pieces to be punched simultaneously or in succession out of the same sample area. The punched out sample pieces are guided through an outlet opening in a lower die by the movement of a punching pin (punch) and in this way transported into a receiving recess in a receiving container, preferably into a well of a microtiter plate. As soon as sample pieces have been punched out of all the desired sample cards and have been received in the receiving container, the analysis of the individual samples contained in the sample pieces can take place by means of methods such as PCR for DNA analyses, high-performance gas chromatography (HPLC) or the like, wherein, for this purpose, further steps, which are not described in detail in the scope of the present application, are carried out after punching out.

A method and a device for automatically punching sample pieces out of sample cards is known for example from U.S. Pat. No. 5,641,682.

Furthermore, a punching device of the abovementioned type is known under the designation "BSD1000-GenePunch" from BSD Robotics (a Luminex Company, in Brisbane, Queensland 4110, Australia). An associated product flyer was available at the following Internet address at the time that the present application was filed: http://www.bsdrobotics.com/Documents/Brochure/BSDR1000(10)%20-%20BSD1000%20GenePunch.PDF.

Furthermore, the mode of operation of this punching device is disclosed in a video film which was available at the following Internet address at the time the application was filed: http://www.bsdrobotics.com/Videos/BSD1000.wmv.

The following mode of operation can be seen from the video film: In the "BSD1000-GenePunch" punching device, a gripper device for sample cards is moved from a magazine, from which the gripper device has removed a sample card, along a horizontally extending rail to a scanner into which the sample card is introduced and subsequently scanned. The gripper device is in this case movable in two directions which are orthogonal to one another, specifically along the rail and orthogonally to the latter, such that the grasped sample card is movable in two dimensions in its card plane. After scanning, the sample card is transported by means of the gripper device to the punching means of the punching device and positioned relative to said punching means, in order that a sample piece can be punched out at that position of the sample card that is evaluated after scanning. The punched-out sample piece is subsequently dispensed into a receiving container, for instance a well of a microtiter plate, arranged under the punching means. In the case of this punching device, a plurality of receiving containers are arranged in a star shape around a rotation axis orthogonal to a horizontal plane, and the position thereof, in particular of a particular well, relative to the punching means takes place by means of a rotary movement and by means of displacement in the horizontal plane. After the punching of one or more sample pieces out of a sample card has been completed, the gripper device transports the punched sample card back along the rail to the card magazine and sets it down there again. The gripper device is then briefly pulled back until the card magazine has been moved upward by one position in order to be able to remove the next sample card from the magazine.

Thus, a punching device known from the prior art generally comprises at least one punching means having a punch and a lower die, wherein the punch is movable between a rest position in which it is away from the lower die and a punching position in which it is close to the lower die, and wherein the punching means has a receiving opening into which a sample card is introducible by means of a movable gripper unit of the punching device and is positionable relative to the punching means. Furthermore, it has a punching drive which is couplable or coupled to the punch of the punching means and by way of which the movement of the punch between the rest position and the punching position is driven.

With the known punching devices, it has been shown that worn punching tools or punching tools that need to be cleaned due to the formation of dust during the punching operation have to be removed in a complicated manner. In this case, in particular a large number of hand movements are necessary in order to uncouple the punching tools (that is to say in particular the punching means having the punch and the lower die) from an associated drive. Furthermore, with such punching devices, it is also difficult to exchange the punching tool easily, when for example sample pieces of a different size (different diameter) are intended to be punched out.

It is therefore the object of the present invention to simplify the handling of the punching tool, in particular the punching means of a punching device.

In order to achieve this object, it is proposed that the punching means comprises a structure separate from the punching device, the punch and the lower die being arranged on said separate structure, wherein the punching means with its structure is configured such that said punching means forms an exchangeable module that is couplable to the punching device and the punching drive.

A common structure, which may also be denoted as a construction or installation, for the punch and the lower die allows optimum exchangeability of the punching means on account of simple removal or insertion of this structure from or into the construction of the rest of the punching device. In this way, it is possible to remove the punching means as a complete module with few hand movements if wear is established or if there is a particular degree of soiling with dust or after a particular number of punching operations. A new punching means module can be inserted immediately, so that the operation of the punching device has to be interrupted only for a very short time. A removed punching means module can then for example be cleaned and maintained for a following use. Single use is also conceivable with such a modular design of the punching means, wherein the punching means is exchanged after a particular operating time and subsequently preferably recycled, for example at the manufacturer. If different sample cards are processed with the punching device, then punching means modules having a different punch size (in particular punch diameter) or having a different number of punches (having associated other lower dies, of course) can easily be inserted and exchanged depending on the sample card to be processed or depending on the method for analyzing punched-out sample pieces. Therefore, the punching device can be used very flexibly and be adapted efficiently for corresponding requirements of a sample analysis, without the operation of the punching device having to be interrupted for a long time due to the exchange of the punching means.

The lower die preferably has a through-passage opening through which the punch passes in its punching position, such that a sample piece punched out of the sample card can be dispensed at an outlet opening into a receiving container arranged beneath the punching means.

Preferably, the receiving container is movable relative to the punching means such that an individual one of a plurality of receiving recesses provided in the receiving container can be arranged beneath the through-passage opening.

In this way, punched-out sample pieces can be received in particular or desired receiving recesses, and so it is possible to unambiguously allocate a punched-out sample piece to a receiving recess in the receiving container. Envisioned as receiving containers are in particular microtiter plates, the individual wells of which form the receiving recesses.

The punching device may comprise a suction device, by means of which dust particles produced during punching are removable in the region of the lower die. Such a suction device counteracts the gathering of dust on the punching means and the entire punching device. Furthermore, the introduction of dust particles into the receiving recesses of a receiving container can be counteracted.

The punching device may furthermore comprise a supply device for deionized air, by means of which deionized air is able to be supplied into the region of the lower die in particular in the region of the outlet opening. Since the punched-out sample card pieces are very small, in particular have a diameter of a few millimeters and generally consist of a coarsely structured fibrous material, for instance filter paper or the like, these sample pieces tend to accumulate on the punch due to of electrostatic charging, and so they cannot be dispensed into a desired receiving recess. Due to the supplied deionized air, it is now possible to produce a gentle air flow in the region between the outlet opening of the lower die and a receiving container, or a particular receiving recess, located beneath the latter, said air flow helping the sample piece to detach from the punch and drop into a respective receiving recess.

To this end, it is furthermore proposed that suction channels and air supply channels are formed separately from one another in the structure of the punching means, with respective connecting points which, in the state in which the punching means is coupled to the punching device, are connected to corresponding suction lines and air supply lines of the punching device. As a result of such a construction of the punching means, the exchangeability thereof can be ensured in spite of the channels that are present for the supply of air and the suction of dust. In this case, the corresponding connections between the punching means and the punching device can also assume further functions, for instance a kind of forced centering or a kind of orientation of the punching means relative to the punching device during the attachment of the punching means to the punching device.

The punching means and the structure thereof are preferably formed such that they are couplable to the punching device, in particular to the punching drive, by means of a substantially horizontally extending movement of the punching means relative to the punching device. In this case, the horizontal movement is understood to be a movement which runs approximately parallel to an underlying surface on which the punching device is placed.

The punching device is in this case preferably configured such that by means of the horizontal movement, the suction channels and air supply channels of the punching means are furthermore couplable to the corresponding suction lines and air supply lines, respectively, of the punching device.

The punching means can furthermore comprise at least one structure coupling means which is able to be brought into engagement with a corresponding counterpart on the punching device, and preferably it can furthermore comprise a drive coupling means provided on the punch, said drive coupling means being able to be brought into engagement with a corresponding counterpart of the punching drive.

In this case, the structure coupling means is preferably configured such that it allows the punching means on the punching device to be releasably locked to the corresponding counterpart on the punching device. In this case, it is further preferred for the locking engagement between the punching means and the punching device to take place automatically by way of the mentioned movement in the substantially horizontal direction.

It is proposed that the structure of the punching means comprises a base which faces the punching device in the coupled state, and also an upper portion, connected to the base and containing the punch, and a lower portion, connected to the base and containing the lower die, wherein the receiving opening is formed between the upper and the lower portions and the upper and lower portions project from the base. The upper and the lower portions can also be regarded as arms of a U-shape, wherein the intermediate space between the arms serves as a receiving opening and the curved part, connecting the arms, of the U-shape corresponds to the base.

In this case, the suction channels and the air supply channels are preferably formed in the lower portion or/and in the base, wherein preferably the suction channels are arranged above the air supply channels in the lower portion.

Preferably, the lower die is received in a sleeve which is fastened to the lower portion, wherein the top side of the sleeve forms a boundary of the suction channel and the underside of the sleeve forms a boundary of the air supply channel for deionized air. The suction channel formed at least partially by the sleeve is in contact with the surroundings upwardly, that is to say in the direction of the punch, by means of suction openings arranged in a distributed manner around the lower die, such that dust particles that accrue on the top side of the lower portion can be extracted by suction in the region of the lower die. The air supply channel has preferably downwardly directed blow-out openings which are likewise arranged in a distributed manner around the lower die, in particular around the outlet opening thereof, the deionized air flowing out of said blow-out openings downwardly, that is to say on the underside of the lower portion.

According to a further independent aspect, the invention relates to an exchangeable punching means module for a punching device for processing dried liquid samples applied to a sample card, in particular bodily liquids such as blood, saliva and the like, wherein the punching means module has a structure on which a movable punch and a lower die are arranged, wherein the punching means module is configured such that it is couplable to the punching device having a punching drive, wherein the punching means module comprises at least one structure coupling means which is able to be brought into engagement with a corresponding counterpart on the punching device, and wherein it furthermore comprises a drive coupling means provided on the punch, said drive coupling means being able to be brought into engagement with a corresponding counterpart of the punching drive.

Preferably, the punching means module can comprise at least one other of the above-described features relating to the punching means.

It is furthermore proposed that the structure of the punching means module is surrounded by a module housing, wherein the structure coupling means and the drive coupling means project beyond the outer side of the housing in order to come into engagement with a corresponding counterpart on the punching device.

According to a further aspect, the invention relates to a metering device, in particular an automated pipetter, having a punching device having at least one of the abovementioned features.

Preferably, in the case of the metering device, a pipetting device having at least one pipetting duct can also be fitted on a movable support having the gripper unit of the punching device.

As an alternative to this, the metering device can have at least two movable supports which are separated from one another, wherein the gripper unit of the punching device is arranged on one support and a pipetting device having at least one pipetting duct is arranged on the other support.

The combination of a metering device with a punching device allows improved automated processing of samples held on sample cards. In a corresponding method for processing sample cards, it is particularly preferred and advantageous for the receiving container, in particular the receiving recesses thereof, to be filled with liquid by means of the metering device before sample pieces are punched out of the sample cards into the receiving recesses. In the case of receiving containers, or receiving recesses, filled with liquid, the risk of sample pieces adhering to the walls of the receiving recesses on account of electrostatic charging is considerably reduced and the punched-out sample pieces generally come into contact with liquid directly after being punched out, become fully saturated therewith and sink in their respective receiving recess in the direction of the lowest point thereof. Within a housing surrounding an overall device of at least one punching device and a metering device, it is also possible for further equipment necessary for carrying out an analysis method to be accommodated, for instance a device for closing the receiving container, a centrifuge or the like. In combination with a metering device, it is also possible that, after sample pieces have been punched out, with regard to the analysis method to be carried out a (further) liquid can be dispensed into the receiving recesses.

The invention is described in the following by way of example and in a nonlimiting manner with reference to the appended figures.

Figure 1:
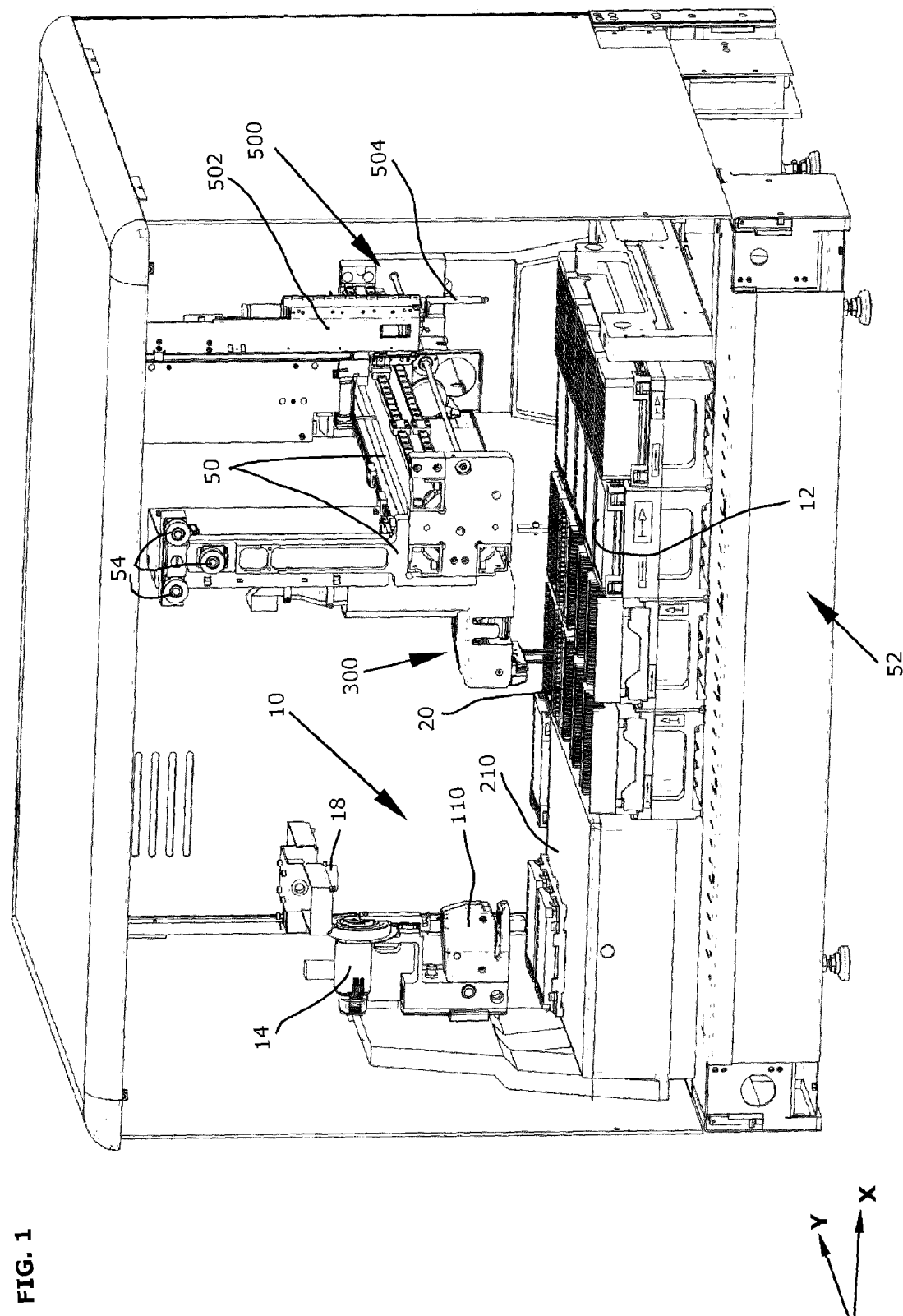
FIG. 1 shows a schematic perspective illustration of a punching device in combination with a metering device.

FIG. 1 shows an overall view of a punching device 10, which is optionally combined here with a metering device 500. In the combination illustrated here, the punching device 10 and the metering device 500 use a common support 50 which is movable in one of the main directions X, Y, Z, namely in the longitudinal direction X. To this end, the support 50 is mounted by means of rollers 54 on longitudinal rails (not illustrated), in the upper region of a support structure 52 which is provided for the overall device but only illustrated in part here. Of course, a drive device (not illustrated) for the support 50 is also present, said drive device being actuable via a control unit (likewise not illustrated) of the overall device.

The metering device comprises a pipetting device 502, fitted on the support 50 so as to be movable in the two other main directions Y, Z, that is to say the transverse direction Y and the vertical direction Z, having at least one pipetting channel 504 for drawing and dispensing liquid into/out of provided receiving containers 12 or a reservoir for the liquid to be metered. The metering device 500 is configured as an automated pipetter, known per se, and will not be described in further detail here.

Fitted on that side of the support 50 that is opposite the pipetting device 502 is a gripper unit 300 which is likewise configured to be movable in the two other main directions Y, Z. This gripper unit 300 should be considered, in the scope of this application, as belonging to the punching device 10, even if in the present example it is fitted on a support 50 that is used jointly with the pipetting device 502. Furthermore, the punching device 10 comprises, as further main components, a punching drive 14, a punching means 110, an image recording device 18 and a receiving plate 210. Furthermore, magazines 20 for in each case a plurality of sample cards 22 (FIG. 3) can be seen in FIG. 1. By means of the gripper unit 300, a sample card is removed from a magazine 20 and fed to the punching means 110, so that by means of the punching means 110 at least one sample piece can be punched out of the respective sample card.

The function of the gripper unit 300 is described only in part in the scope of this application. For details concerning the configuration of the gripper unit and the interaction thereof with the punching device or the punching means of the present application, reference is made to the application, filed simultaneously by the applicant, having the title "Punching device having a gripper unit" (application number DE102011XXXXXX.X), the content of which is incorporated here by reference with respect to the configuration of the gripper unit.

Likewise, in the scope of this application, special features of the receiving plate 210 are only dealt with in part. For details concerning the configuration of this receiving plate or of a drive (not visible in FIG. 1), covered by the receiving plate 210, for positioning receiving containers relative to the punching means 110, reference is made to the two simultaneously filed applications with the title "Punching device with receiving plate" (application number DE102011XXXXXX.X) and "Punching device with illuminated receiving plate" (application number DE102011XXXXXX.X), the content of both of which is incorporated here by reference with respect to the configuration of the receiving plate and the drive covered by the latter.

Figure 2:
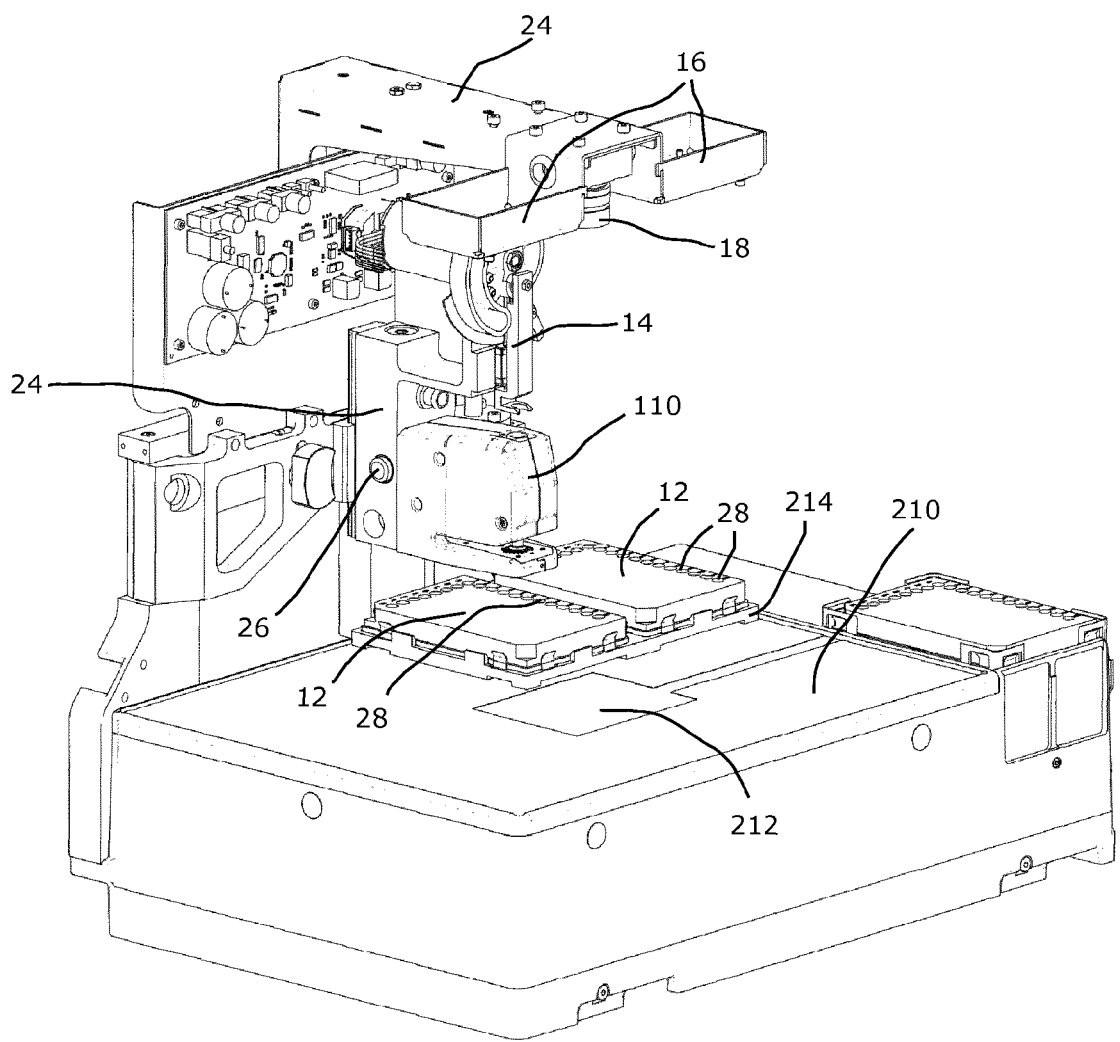
FIG. 2 shows a schematic perspective illustration of the punching device without a metering device and without a gripper unit.

FIG. 2 shows a schematic perspective illustration of the punching device 10 without a gripper unit 300. The punching device 10 comprises a frame-like structure or support structure 24, to which the punching drive 14 and the image recording device 18 are fastened, and on which the punching means 110 is fitted in a removable manner as a punching means module. FIG. 2 shows the state in which the modular punching means 110 is coupled to the structure 24 of the punching device. In order to be able to remove the punching means 110 from the structure 24, it is proposed that an actuating element or push button 26 can be actuated so that an engagement between the punching means 110 and the support structure 24 can be released. The receiving plate 210 serves for mounting or supporting at least one receiving container 12, which is preferably provided as a microtiter plate having a particular number of wells (receiving recesses) 28. It is also possible for different microtiter plates to be used, and the number of wells 28 is not limited per se, except with regard to the fact that a sample piece punched out of a sample card has space in a corresponding well 28.

It is also apparent from the overview illustration in FIG. 2 that the image recording device 18 is arranged substantially vertically above an illuminated area 212 of the receiving plate 210. This illuminated area 212 is formed preferably by an electroluminescent film received in the receiving plate or arranged on the rear side thereof. A microtiter plate 12 arranged thereon can be backlit by the EL film 212, such that an image of the backlit microtiter plate 12 or of a part thereof can be captured by the image recording device 18. The microtiter plate(s) 12 is/are received on the receiving plate 210 in a transport frame 214 which is coupled via magnets (not illustrated here) to a drive unit located under the receiving plate 210 and can be moved on the receiving plate 210 relative to the stationary punching means 110 by means of this drive unit. As a result, a particular receiving recess 28 of a receiving container 12 can be arranged precisely beneath the punching means 110, such that a punched-out sample piece drops into this receiving recess or is received in the latter. Provided on both sides of the image recording device 18 are holders 16 for alternative illumination means, which illuminate from above an article, preferably a sample card, positioned under the image recording means 18, so that image-processing processes can be carried out for the sample card, for example recognition of a bar code or the like.

Figure 3A:
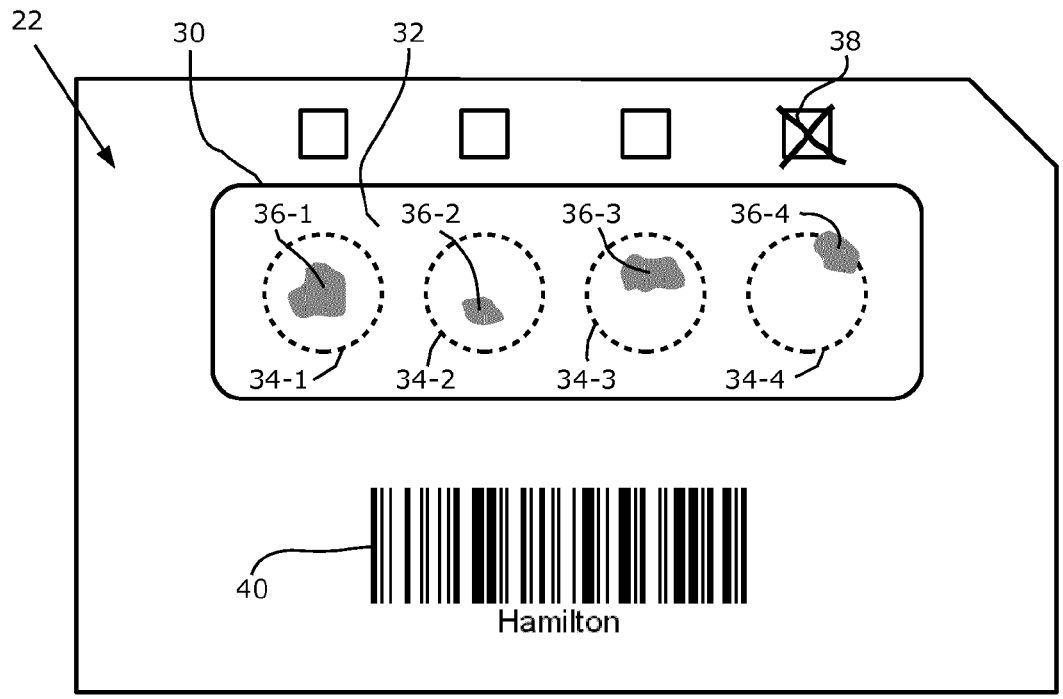
FIG. 3 shows, in partial figures a) and b), schematically illustrated sample cards in the state prior to the punching out of sample pieces (FIG. 3a) and after the punching out (FIG. 3b).
Figure 3B:
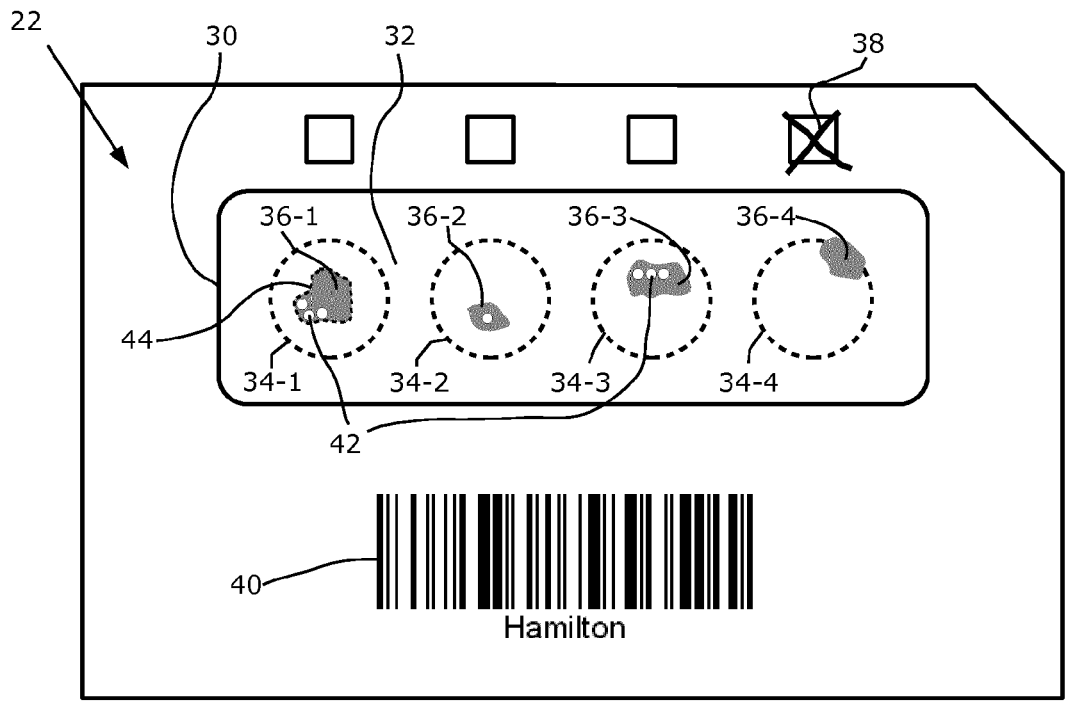

FIG. 3 shows, in partial figures a) and b), an example of a sample card 22. The sample card has a kind of opening 30, in which an absorbent material 32, for instance a kind of filter paper or the like is visible. At least one sample area is identified on the absorbent material, and in the present case there are four such sample areas 34-1 to 34-4, which are illustrated as dashed circles. If samples, such as blood, saliva or other liquids are collected by means of the sample card 22, the liquid samples are intended to be deposited as far as possible within the marked sample areas 34-1 to 34-4. In the present example, samples 36-1 to 36-4 of different sizes, for example drops of blood or samples of saliva, have been deposited in the corresponding sample areas 34-1 to 34-4. The sample 36-4 is in this case not located completely within the marking of sample area 34-4, and so this sample has correspondingly been indicated as invalid by a sample donor or by a member of medical staff by way of a cross 38 above the sample area 34-4. A code (bar code, 2D bar code or the like) 40 is also provided on the card beneath the absorbent material 32, in order to allow the sample card to be identified and to be assigned to a sample donor, a collecting institute or the like. Further information, such as manufacturer's information, information regarding the purpose of the card or regarding the sample liquid, etc. may also be contained or printed on the sample card 22. The samples 36-1 to 36-4 applied in liquid form are absorbed by the absorbent material 32 and subsequently dry. After drying, sample pieces can be punched out of the samples 36-1 to 36-4 by means of the punching means 110. After a plurality of sample pieces have been punched out of the samples 36-1 to 36-3, the sample card 22 is indicated in FIG. 3b by the white punched holes 42. Where and in what order sample pieces were punched out can be established for example by means of image processing, wherein it is firstly possible to detect whether a sample is located within the marked sample area 34-1 to 34-4 (for example by using the cross 38), where the sample 36-1 to 36-4 is located within the sample area 34-1 to 34-4, and what boundary it has, this being indicated by the dashed line 44 in the case of the sample 36-1. Using such information and the desired number of sample pieces to be punched out, it is possible to identify where sample pieces should be punched out. Accordingly, the sample card 22 can then be positioned relative to the punching means so that the sample pieces can be punched out at the predetermined points. The form illustrated here of the sample card is purely by way of example, and the sample card can have some other format, more or fewer, smaller or larger sample areas 34, etc.

Figure 4:
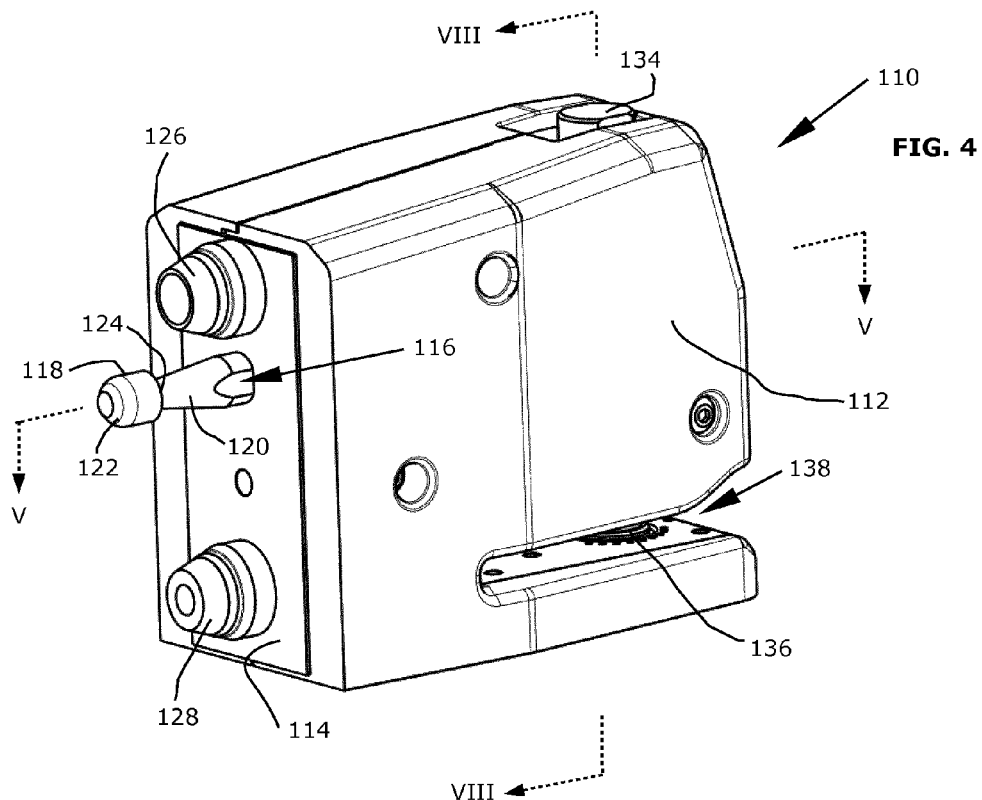
FIG. 4 shows a schematic perspective illustration of a modular punching means of the punching device obliquely from the rear.
Figure 5:
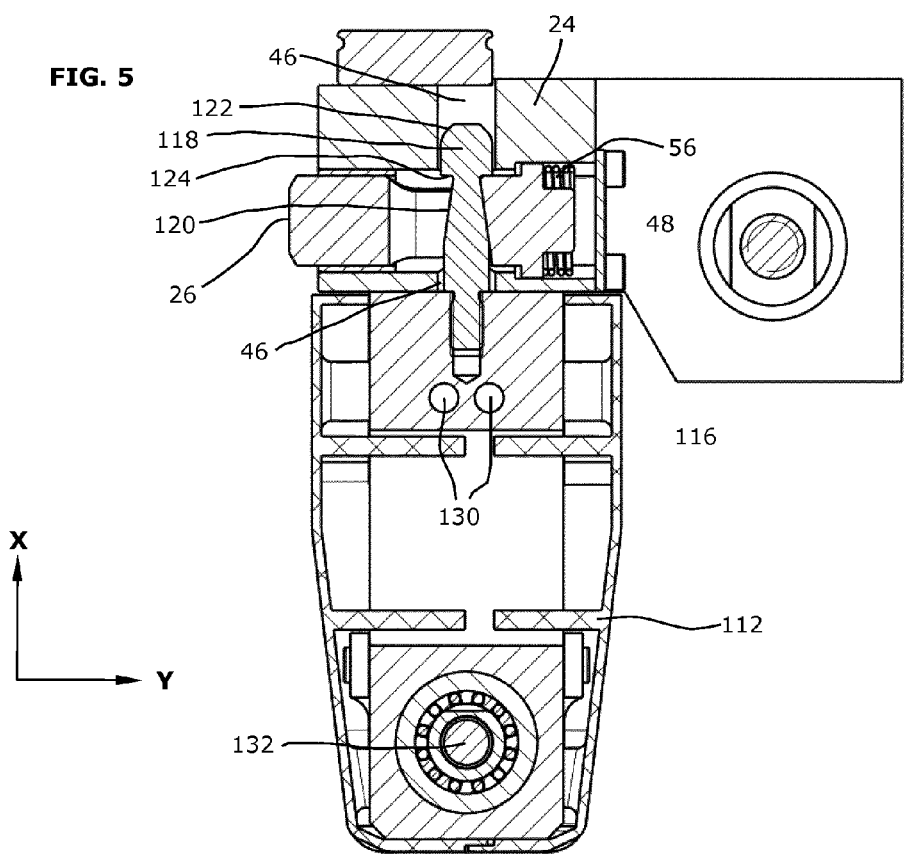
FIG. 5 shows a schematic sectional illustration of the punching means along the section line V-V in FIG. 4 with a counterpart, serving for coupling, of the punching device.

FIG. 4 shows an embodiment of a punching means 110, of modular configuration, in its punching means housing 112. On the rear side 114, which faces the punching device 10 in the coupled state of the structure 24, the punching means 110, which may also be denoted as a punching head, has a coupling pin 116 (structure coupling means) having a coupling head 118 and a coupling shank 120 which is formed with an at least partially narrowing diameter. The coupling head 118 has a frustoconical front portion 122 which allows the coupling pin 116 to be introduced easily into a corresponding coupling opening 46 on the support structure 24 of the punching device 10, this being visible from the sectional illustration of FIG. 5 (corresponding to the section line V-V in FIG. 4). Formed at the transition from the coupling head 118 to the coupling shank 120 is a setback 124 which is in engagement with a spring-preloaded latching element 48 in the state coupled to the structure 24, such that the punching means 110 can be locked to the support structure 24 or fitted on the support structure 24 in a locked state. In order to release this engagement, the latching element 48 can be moved in the Y direction counter to the force of a spring 56 by means of the push button 26 already mentioned with reference to FIG. 2, such that the punching means module 16 can be removed from the structure 24 in the X direction. The punching means 16 is likewise coupled to the structure 24 substantially in the horizontal direction X, wherein the shaping of the coupling head 118 and latching element 48 allows the latching element 48 to be moved counter to the preloading force of the spring 56 until the latching element 48 can engage behind the coupling head 118 at the setback 124 and rests at least partially against the coupling shank 120 (FIG. 5).

On the rear side 114 of the punching means module 110 (FIG. 4), a connection piece 126 for coupling to a suction device (not illustrated) and a further connection piece 128 for connecting to a device (not illustrated) for supplying deionized air can furthermore be provided. In the coupled state, these connection pieces 126, 128 are connected in a fluid-tight manner to corresponding counterparts and lines on the structure 24 of the punching device. Two lines or suction channels 130 which are connected to the suction connection piece 126 can be seen in FIG. 5.

Figure 6:
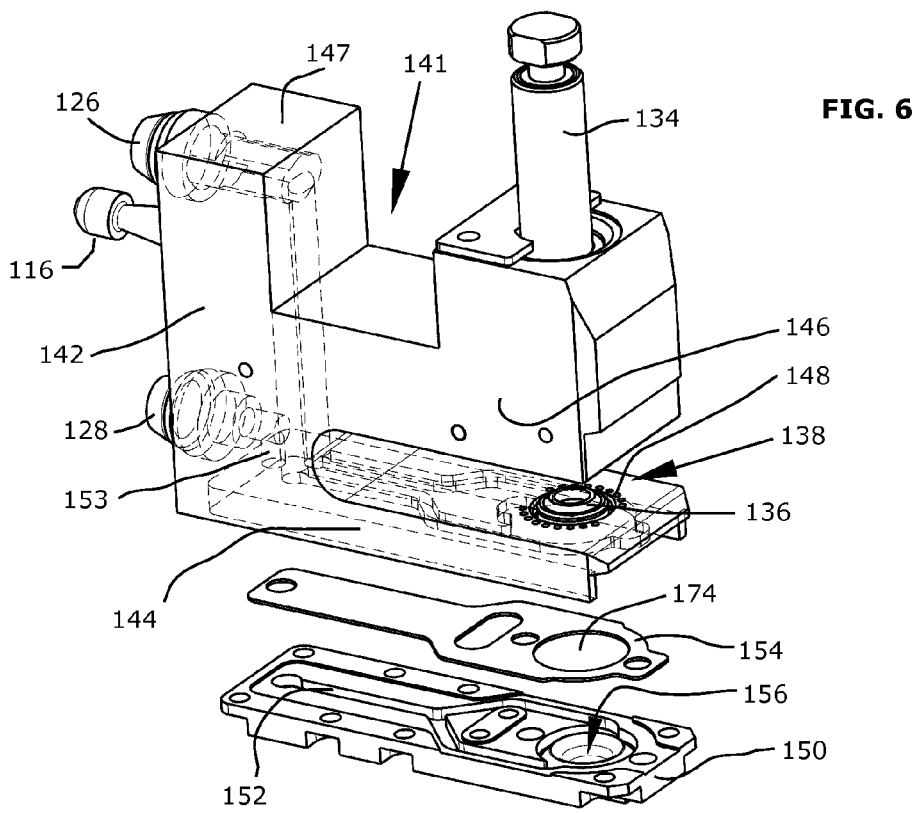
FIG. 6 shows a schematic, perspective exploded illustration of a lower portion of the punching means.

FIG. 6 illustrates the punching means 110 without a housing and it can be seen that it has its own structure or construction 141, with a base 142, a lower portion 144 and an upper portion 146. The lower portion 144 and the upper portion 146 are connected to the base 142 and have the receiving opening 138 between one another. The two portions 144, 146 form, together with the base 142, a kind of U-shape, wherein the upper portion 146 is arranged in a manner offset somewhat downwardly in the direction to the lower portion 144 with respect to an upper edge 147 of the base 142.

Figure 7A:
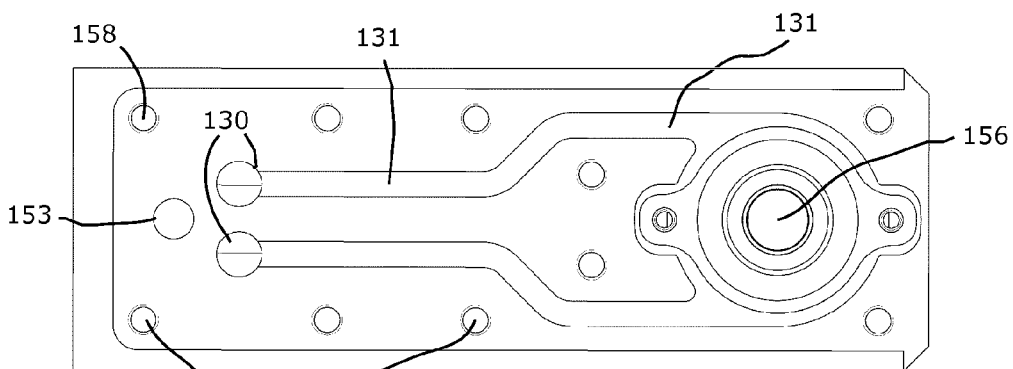
FIG. 7 shows, in partial figures a) and b), the configuration of channels in the lower portion of the punching means for suction of dust (FIG. 7a) and for supplying deionized air (FIG. 7b).
Figure 7B:
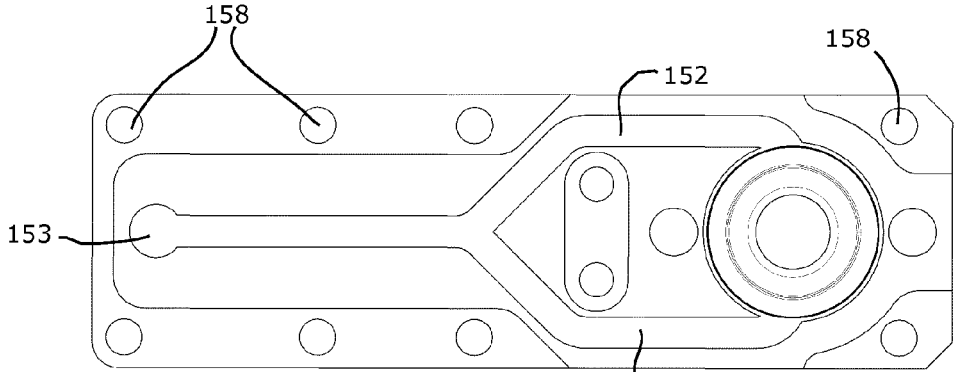

The lower die 136 can be seen on the top side of the lower portion 144. Provided in a manner distributed around the lower die are suction openings 148 which are connected to suction channels 131 (FIG. 7b) provided in the lower portion 144 and to the suction channels 130 extending vertically in the base 142. Dust that is produced during punching can be extracted by suction through the suction openings 148 and be introduced into a collecting container (not illustrated) of a suction device of the punching device 10. The lower portion 144 furthermore comprises an insert 150 in which channels 152 for supplying deionized air toward the underside of the lower portion 144 are provided. The channels 152 are covered with respect to the suction channels 131 by a separating plate 154. The channels 152 are connected to the corresponding connection piece 128 via a vertically extending channel piece 153. An outlet opening 156, through which a sample piece punched out of a sample card can pass downwardly in the direction of a receiving container 12 (FIG. 2), can furthermore be seen in the insert 150 of the lower portion 144. The insert 150 is preferably screwed to the rest of the lower portion 144 at a number of points 158. The channels 130, 131 for suction and the channels 152, 153 for supplying deionized air are preferably formed integrally in the lower portion 144 and the associated insert 150, respectively, and they are preferably milled/drilled channels or molded parts which have been produced by an injection-molding or casting method.

Figure 8:
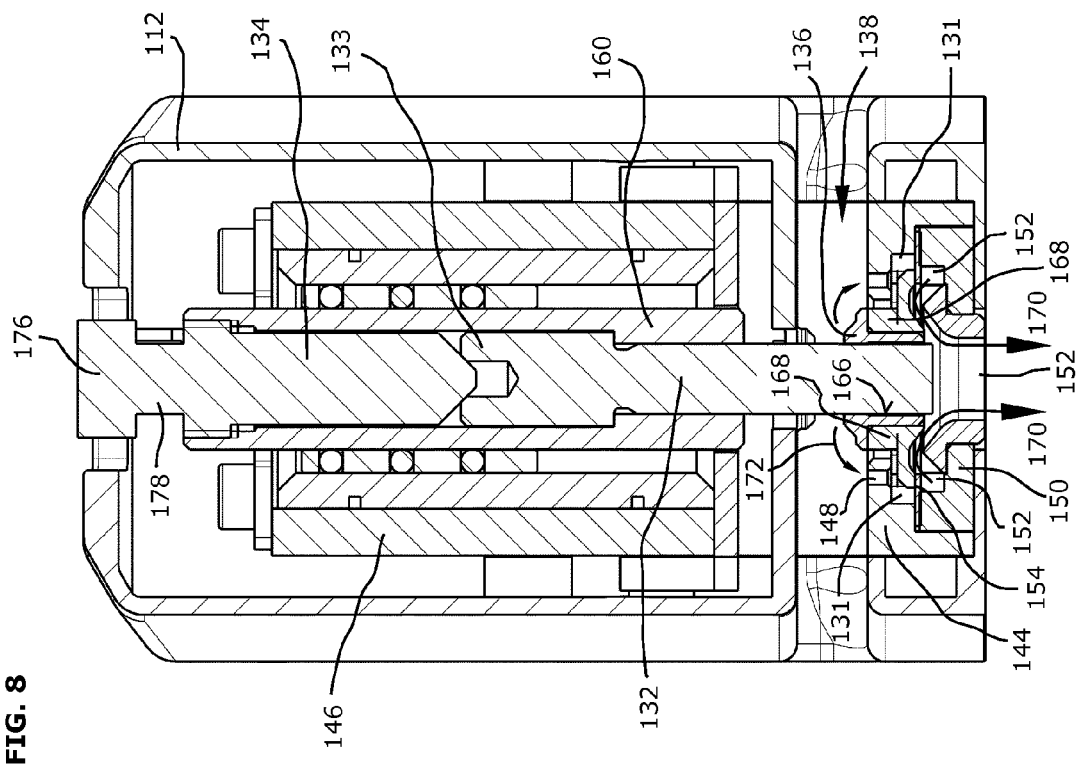
FIG. 8 shows a sectional illustration of the punching means along a section line VIII-VIII in FIG. 4.

FIG. 8 shows a sectional illustration of the punching means 110 corresponding to the section line VIII-VIII in FIG. 4. The following components which have already been mentioned can be seen in this illustration: Housing 112, lower portion 144, upper portion 146, insert 150, receiving opening 138 and lower die 136. The punching means 110 furthermore comprises a punch 132, the upper end 133 of which is adjoined by a preferably pin-like drive coupling means 134. The punch and the drive coupling means 134 are received in a common sleeve 160 which is connected in such a way to the punch 132 and the drive coupling means 134 that it is movable back and forth together with the latter two in the longitudinal direction thereof (Z direction, when the punching means 110 is fitted on the punching device 10). The sleeve 160 is surrounded by a ball bearing or ball cage 162 which allows the sleeve 160 to move relative to a stationary sleeve 164 which is connected fixedly to the upper portion 146 of the structure 141 of the punching means 110.

The lower die 136 has a through-passage opening 166 for the punch 132, said through-passage opening 166 opening into the outlet opening 156. The lower die 136 is received in a sleeve 168 which is formed such that it separates the suction channels 131 and the channels for deionized air 152 from one another in the region of the lower die 136 and guides the respective air flows in a corresponding manner, this being indicated by the arrows 170 for the deionized air and by means of the arrows 172 for the suction through the suction openings 148. In the region of the lower die, the sleeve 168 and the separating plate 154 interact in a suitable manner such that the two flows for the suction of dust and for supplying deionized air are separated from one another, with the sleeve 168 resting preferably on the separating plate 154 and at least partially covering an opening 174 (FIG. 6) provided in the separating plate 154. Of course, at those points at which the punch 132 can move from the upper portion into the lower portion and in the direction of the outlet opening 156, the housing 112 also has corresponding openings which allow the punch 132 to pass through.

Figure 9:
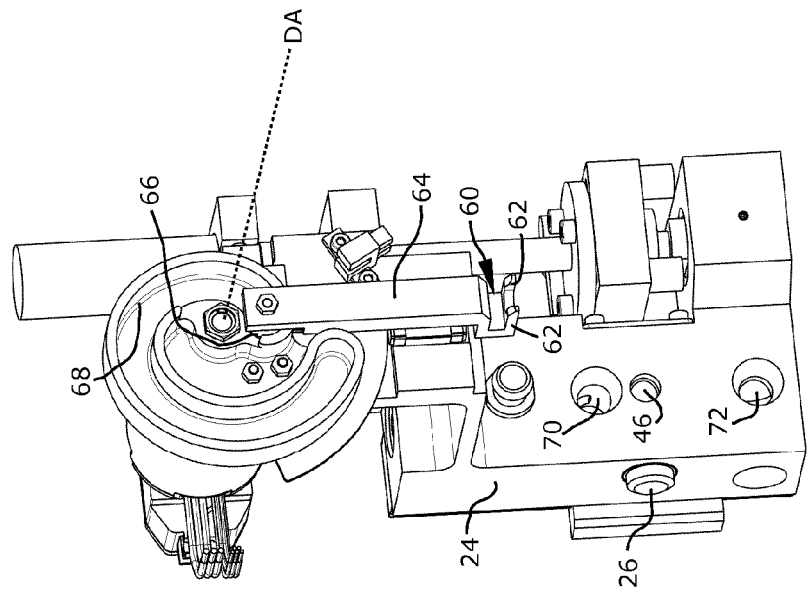
FIG. 9 shows a schematic perspective illustration of a punching drive couplable to the punching means.

The drive coupling means 134 has a coupling head 176 in its upper region and a coupling neck 178 which has a smaller diameter. The coupling head 176 and the coupling neck 176 are introducible into a correspondingly formed drive-side coupling counterpart 60 (FIG. 9). The coupling counterpart 60 has two fork-like prongs 62 which are preferably arranged at such a distance from one another that the coupling neck 178 can be accommodated between them, and the coupling head 176 rests on them by way of its underside. By way of this form-fitting connection, the drive coupling means 134 and thus the punch 132 connected thereto can be moved between its rest position and its punching position by means of the punching drive 14. The coupling counterpart 60 is provided at the lower end of a drive rod 64 at the top end of which a roller 66 is fitted. The roller 66 is received in a slotted guide means 68 which extends in a spiral shape. If this slotted guide means 68 is set in rotation, for example in the clockwise direction in FIG. 9, by means of a motor (not illustrated here), in particular an electric motor, the drive rod 64 is moved linearly downward due to the slotted guide 68 moving away from the rotation axis DA, this causing the punch 132 to move from its rest position into the punching position illustrated in FIG. 8.

It is furthermore apparent from FIG. 9 that the punching drive 14 is fitted on the support structure 24 of the punching device. Beneath the punching drive, connection openings 70 and 72 can be seen in the structure 24, it being possible to introduce the connection pieces 126 and 128 of the punching means module 110 into said connection openings 70 and 72. Furthermore, the coupling opening 46 already mentioned with reference to FIG. 5 can be seen beneath the connection opening 70, it being possible to introduce the coupling pin 116 into said coupling opening 46.

The punching means module 110 has its own structure 141 which is separate from the structure 24 of the punching device and comprises the punch 132 and the lower die 136. The two separate structures 24 and 141 can be connected releasably together via a coupling pin 116 provided on the punching means module 110 and a latching element 48 provided on the structure 24 of the punching device 10. In this case, when the two structures 24, 141 are coupled, in principle the drive coupling means 134, in particular the coupling head 176 and coupling neck 178 thereof, can simultaneously be coupled to the coupling counterpart 60. Furthermore, as a result of the structural coupling, a substantially simultaneous connection of the channels 130, 131, 152, 153 provided in the punching means module 110 to corresponding connection lines in the punching device also takes place. Thus, overall, as a result of the modular design of the punching means 110 (punching head), simplified exchangeability is enabled, and so, with few hand movements, the punching means 110 can be fitted to the punching device 10 for the purpose of operation and can be removed therefrom for the purpose of maintenance/exchange.

The invention claimed is:
1. A punching device for processing dried samples applied to a sample card, comprising:
a support structure;

at least one punching head removably coupled to the support structure, the at least one punching head having a punch and a lower die, wherein the punch is movable between a rest position in which the punch is away from the lower die and a punching position in which the punch is close to the lower die, and wherein the punching head has a receiving opening into which a sample card is introducible by a movable gripper unit of the punching device and the moveable gripper unit is positionable relative to the punching head, a punching drive fastened to the support structure, wherein the punching drive is couplable or coupled to the punch of the punching head and is configured to drive the movement of the punch between the rest position and the punching position, wherein the punching drive has a first structure and the punching head has a second structure that is separate from the first structure of the punching drive, wherein the punch and the lower die are arranged on said second structure, wherein the second structure of the punching head is configured such that said punching head forms an exchangeable module that is couplable to the punching drive, an actuating element operable to release an engagement between the punching head and the support structure; and a suction device configured to be coupled to the punching head such that dust particles produced during punching are removable in the region of the lower die, wherein the punching head comprises suction channels formed in the second structure of the punching head.

2. The punching device as claimed in claim 1, wherein the punching device further includes a receiving container and the lower die has a through-passage opening through which the punch passes in its punching position, such that a sample piece punched out of the sample card can be dispensed at an outlet opening into the receiving container arranged beneath the punching head.

3. The punching device as claimed in claim 2, wherein the receiving container has a plurality of receiving recesses and is movable relative to the punching head such that an individual one of the plurality of receiving recesses provided in the receiving container can be arranged beneath the through-passage opening.

4. The punching device as claimed in claim 1, further comprising a supply device for deionized air, configured such that deionized air is able to be supplied into the region of the lower die.

5. The punching device as claimed in claim 4, wherein the region of the lower die is a region of an outlet opening.

6. The punching device as claimed in claim 1, wherein air supply channels are formed separately from the suction channels in the second structure of the punching head, with respective connecting points which, in the state in which the punching head is coupled to the punching device, are connected to corresponding suction lines and air supply lines of the punching device.

7. The punching device as claimed in claim 6, wherein the suction channels and air supply channels of the punching head are furthermore couplable to the corresponding suction lines and air supply lines, respectively, of the punching device by a horizontal movement.

8. The punching device as claimed in claim 6, wherein the suction channels and the air supply channels are formed in a lower portion or/and in a base of the second structure of the punching head.

9. The punching device as claimed in claim 8, wherein the lower die is received in a sleeve which is fastened to the lower portion, wherein a top side of the sleeve forms a boundary of the suction channels and an underside of the sleeve forms a boundary of the air supply channels for deionized air.

10. The punching device as claimed in claim 8, wherein the suction channels are arranged above the air supply channels in the lower portion.

11. The punching device as claimed in claim 1, wherein the punching head and the second structure thereof are formed such that the punching head is couplable to the punching drive, by a substantially horizontally extending movement of the punching head relative to the punching drive.

12. The punching device as claimed in claim 1, wherein the second structure of the punching head comprises a base which faces the punching device in the coupled state, as well as an upper portion, connected to the base and containing the punch, and a lower portion, connected to the base and containing the lower die, wherein the receiving opening is formed between the upper and the lower portions and the upper and lower portions project from the base.

13. A metering device comprising an automated pipetter having a pipetting device with at least one pipetting duct and having a punching device as claimed in claim 1.

14. The metering device as claimed in claim 13, wherein the pipetting device is fitted on a movable support having the gripper unit of the punching device.

15. The metering device as claimed in claim 13, which has at least two movable supports which are separated from one another, wherein the gripper unit of the punching device is arranged on one support and the pipetting device having at least one pipetting duct is arranged on the other support.

16. The punching device as claimed in claim 1, wherein the punching device is operable to process liquid samples including bodily fluids.

* * * * *